United States Patent
Kross et al.

(10) Patent No.: US 11,439,606 B2
(45) Date of Patent: Sep. 13, 2022

(54) REDUCTION OF HYPERGLYCEMIA BY ADMINISTRATION OF DIMETHYLFORMAMIDE FOR TREATING HYPERGLYCEMIC CONDITIONS, INCLUDING DIABETES MELLITUS

(71) Applicants: Robert D. Kross, Bellmore, NY (US); Guadalupe Cleva Villanueva Lopez, Mexico City (MX)

(72) Inventors: Robert D. Kross, Bellmore, NY (US); Guadalupe Cleva Villanueva Lopez, Mexico City (MX)

(73) Assignee: Guadalupe Cleva Villanueva Lopez, Cuidad de Mexico (MX), part interest ( * ) Notice: Subject to any disclaimer, the term of this patent is extended or adjusted under 35 U.S.C. 154(b) by 184 days.

(21) Appl. No.: 16/699,674

(22) Filed: Dec. 1, 2019

(65) Prior Publication Data

US 2020/0170969 A1    Jun. 4, 2020

Related U.S. Application Data

(60) Provisional application No. 62/917,291, filed on Dec. 3, 2018.

(51) Int. Cl.
  *A61K 31/16*   (2006.01)
  *A61K 9/00*    (2006.01)
  *A61P 3/10*    (2006.01)

(52) U.S. Cl.
  CPC ............ *A61K 31/16* (2013.01); *A61K 9/0053* (2013.01); *A61K 9/0095* (2013.01); *A61P 3/10* (2018.01)

(58) Field of Classification Search
  CPC .... A61K 31/16; A61K 9/0095; A61K 9/0053; A61K 9/00; A61P 3/10
  See application file for complete search history.

(56) References Cited

U.S. PATENT DOCUMENTS

2014/0349926 A1    11/2014   Prestrelski et al.

OTHER PUBLICATIONS

P.C.T. International Search Report, dated Feb. 12, 2020, Prepared by the U.S. International Searching Authority (ISA/US).
Cohut, "Diabetes: The insulin pill may finally be here," Medical News Today, Published Jun. 26, 2018 (See, Entire Document, especially p. 5, ¶¶ 3-4).
Mendoza-Betancourt et al., "Dimethlylformamide Reduces Cerebral Ischaemia in Diabetic Rats Hours," Free Radicals, Antioxidants and Diseases, (Aug. 2018) (Entire Document).

*Primary Examiner* — Sun Jae Yoo
(74) *Attorney, Agent, or Firm* — Edwin D. Schindler

(57) ABSTRACT

A treatment for a hyperglycemic condition, including diabetes mellitus, includes the step of administering to a human being dimethylformamide ("DMF"), which has the chemical structural formula:

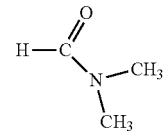

Figure 1:
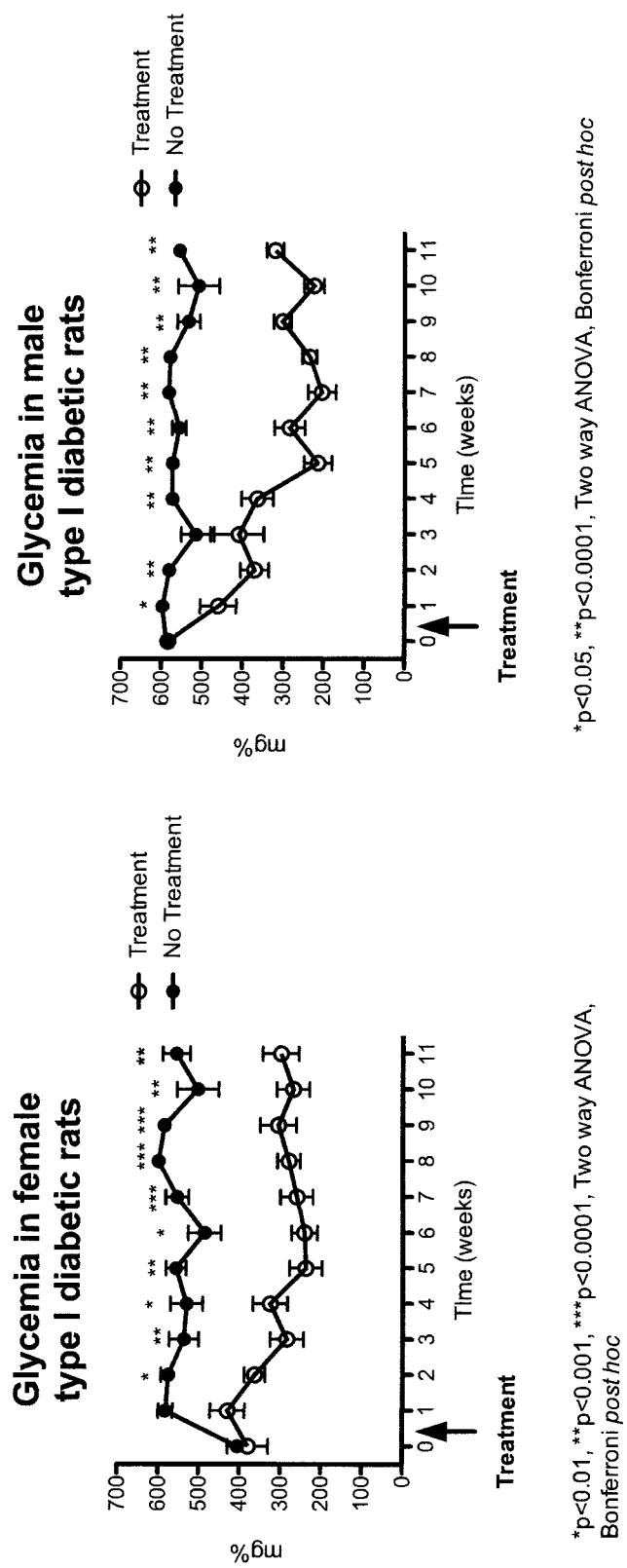

DMF can be administered to the human patient in a wide variety of ways, however it is preferable that the administration of DMF be performed orally and the dose of DMF could be combined with numerous inert substances known to the prior art, such as a sugarless fruit juice concentrate. The preferred daily dosage of DMF administered to a person would be about 0.041 mg/kg body weight to about 1.23 mg/kg of body weight of the person.

7 Claims, 5 Drawing Sheets

REDUCTION OF HYPERGLYCEMIA BY ADMINISTRATION OF DIMETHYLFORMAMIDE FOR TREATING HYPERGLYCEMIC CONDITIONS, INCLUDING DIABETES MELLITUS

CROSS-REFERENCE TO RELATED APPLICATION

The inventor claims domestic priority, pursuant to 35 U.S.C. § 119(e), on the basis of U.S. Provisional Patent Application No. 62/917,291, filed Dec. 3, 2018, the entire disclosure of which shall be deemed to be incorporated by reference herein.

BACKGROUND OF THE INVENTION

Technical Field of the Invention

The present invention relates, generally, to a method for the reduction of glycemia in hyperglycemic conditions in humans.

More particularly, the present invention related to a method for the reduction of glycemia in hyperglycemic conditions in humans, including diabetes mellitus, shock, drug-induced hyperglycemia or associated hyperglycemia and hyperglycemic repercussions, through the administration of dimethylformamide.

Description of the Prior Art

It is generally known in the prior art that the structural formula of certain medications, currently used in the treatment of diabetes, share certain guanide and biguanide structural characteristics, which are shown below:

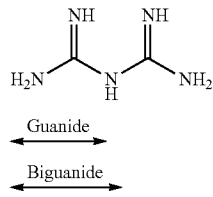

Guanide
Biguanide

It further appears that compounds that have been used in the treatment of diabetes, such as metformin (a biguanide) share the common structure of a [C—N—C=N] configuration shown by the circled bonds in the guanide configuration below:

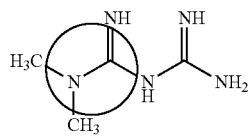

Pharmaceuticals used in the treatment of diabetes and related conditions, such as metformin, are known to have common side effects that include nausea, vomiting, upset stomach, diarrhea, weakness, or a metallic taste in the mouth. More serious side effects from metformin and chemically similar drugs, in rare circumstances, include lactic acidosis and, for this reason, the United States Food and Drug Administration ("FDA") requires that metformin carry a "black box" warning, which is the most severe or serious warning that the FDA assigns to prescription pharmaceuticals.

Similarly, levamisole, another drug having a wide variety of uses, including having once been used in the treatment of hyperglycemia, was withdrawn from the United States market in 2000, due to its ability to cause numerous serious adverse effects, including agranulocytosis.

An effective and potentially safer treatment for hyperglycemia, including diabetes mellitus, is therefore desirable, particularly for patients not able to tolerate continued use of metformin and related pharmaceuticals currently available for the treatment of hyperglycemia-related conditions.

SUMMARY OF THE INVENTION

It is, therefore, an object of the present invention to provide a method for the treatment of hyperglycemic conditions, including diabetes mellitus that is effective and avoids the more severe side effects attendant treatments for hyperglycemic conditions currently known to the state of the art.

It is a further object of the present invention to provide a method for the treatment of hyperglycemic conditions, including diabetes mellitus that can be orally administered to a patient, or taken by a patient, with ease.

It is an additional object of the present invention to provide a method for the treatment of hyperglycemic conditions, including diabetes mellitus that overcomes the inherent disadvantages of treatments known to the state of the art.

The foregoing and related objects are accomplished by the present invention for the treatment of hyperglycemic condition, including diabetes mellitus, which provides a method for administering to a human being dimethylformamide ("DMF"), which has the chemical structural formula:

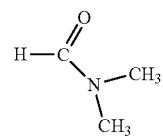

In accordance with the present invention, DMF can be administered to the human patient in a wide variety of ways, however it is preferable that the administration of DMF be performed orally, which would be both effective and convenient for medical personnel and the patient, and which could be combined with numerous inert substances known to the prior art. It has been determined that the preferred dosage of DMF administered to a person would be approximately 0.041 mg/kg body weight to approximately 1.23 mg/kg of body weight of the patient on a daily basis.

It is acknowledged that DMF, per se, has an unpleasant odor (e.g., an amine-like fishy taste) and is likely unpalatable unless mixed or dissolved in one or more inert substances, though, the preferred route for administering is orally. It is preferred that the DMF is dissolved in a flavorful solution base, e.g., a sugar-free fruit juice concentrate, or a sugar-free acidic liquid, which may include citric and/or malic acids. The inclusion of a fruit juice concentrate would require an appropriate food preservative, e.g., sodium benzoate, though other inert solvents and other types of preservatives may be used and are well within the scope of the present invention.

Further, a controlled test conducted with type I diabetic female and male rats has discovered, as detailed hereinafter, the method of the present invention yields a beneficial reduction of triglycerides and improved kidney and liver function and, apparently, in some cases below that which can be expected from non-diabetic rats.

BRIEF DESCRIPTION OF THE DRAWING FIGURES

Figure 2:
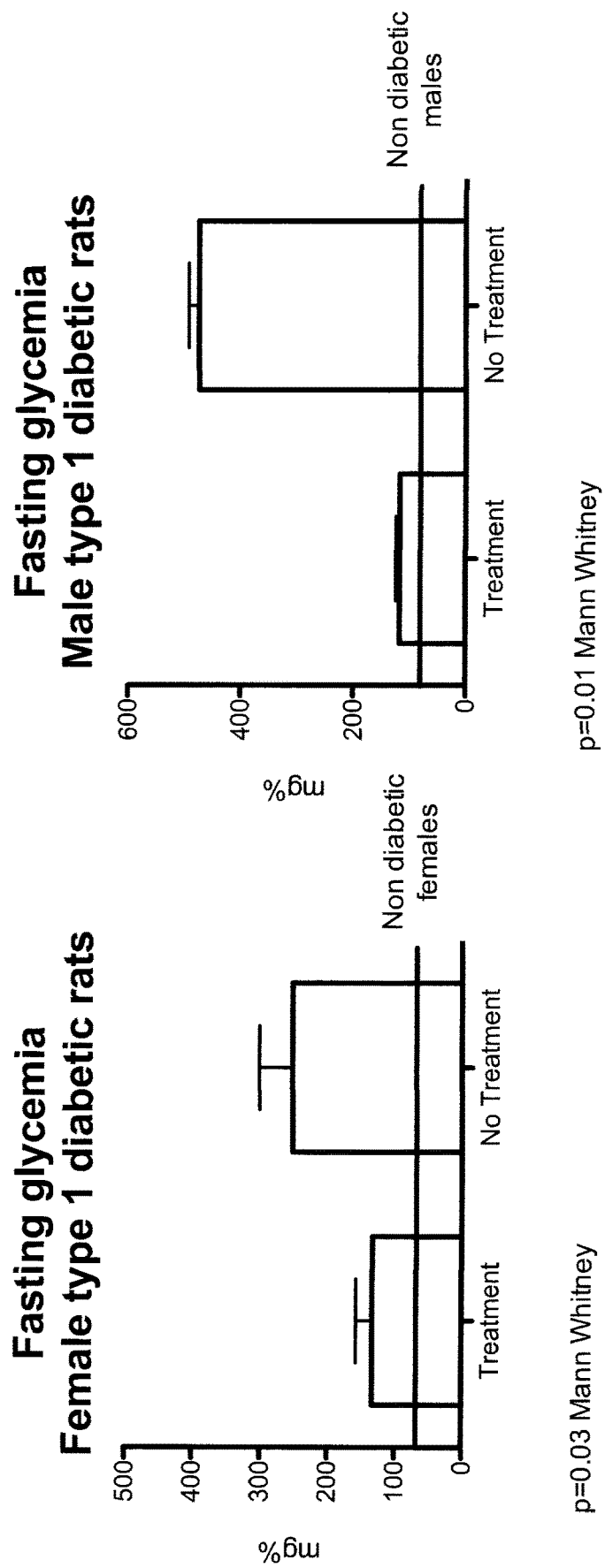
Figure 3:
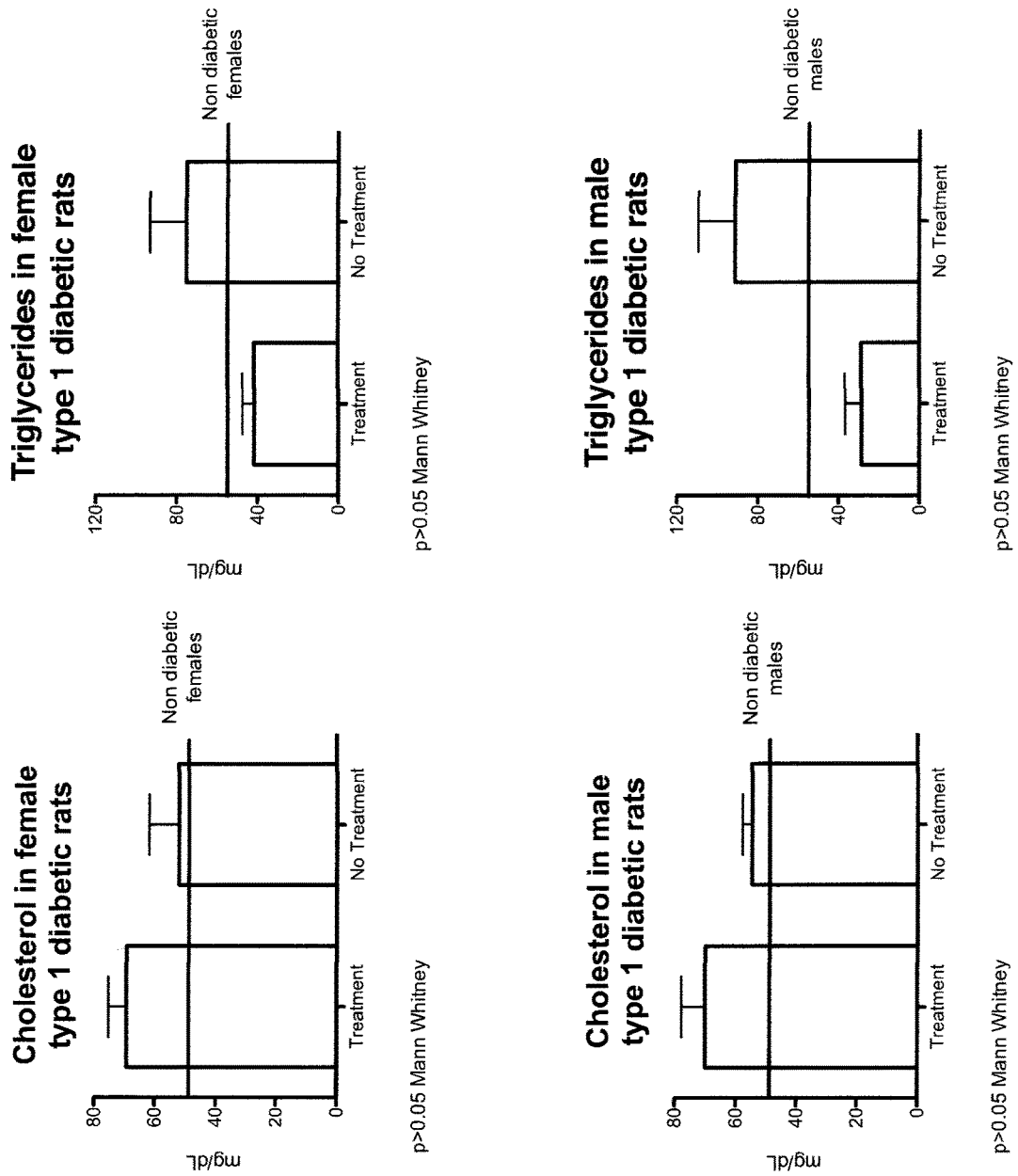
Figure 4:
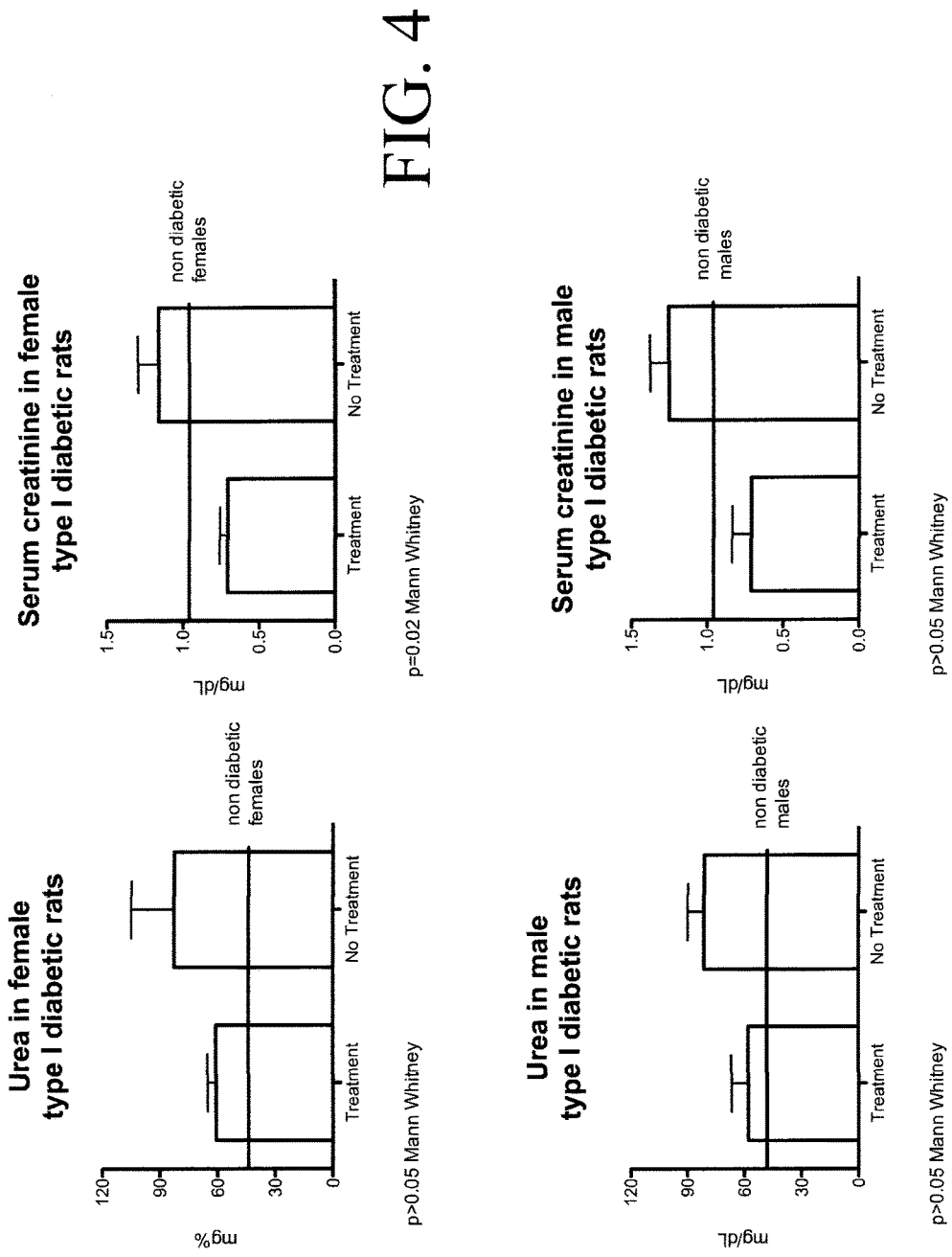
Figure 5:
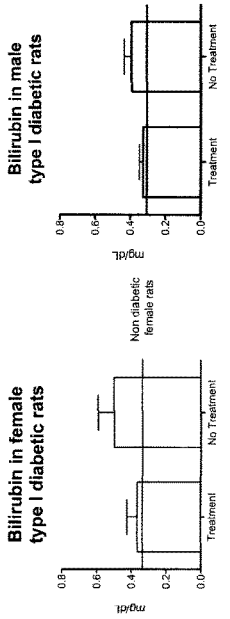
Figure 5:
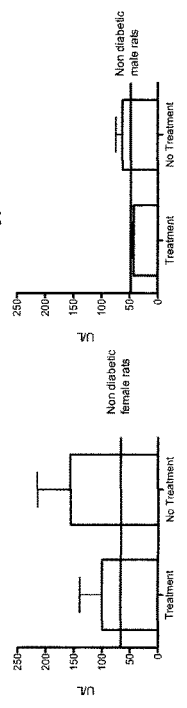
Figure 5:
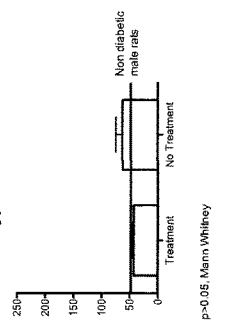
Figure 5:
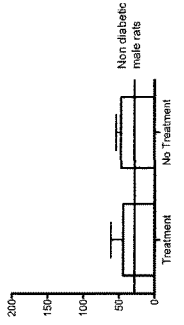
Figure 5:
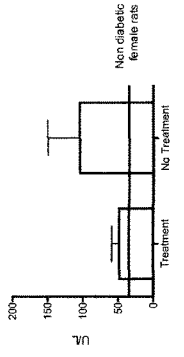
Figure 5:
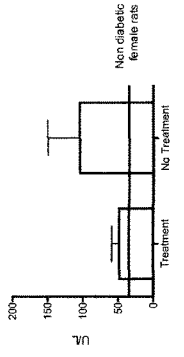
Figure 5:
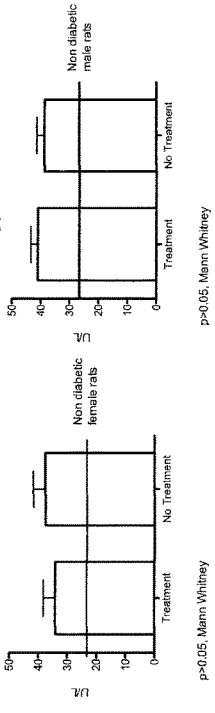
Figure 5:
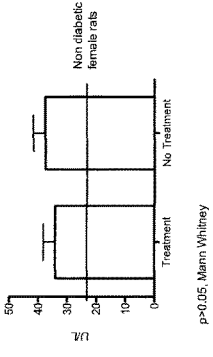

In the drawing:

FIG. 1 graphically shows the results of the effectiveness of treating hyperglycemia in female and male rats having type I diabetes with DMF against a control group in which female and male rats having type I diabetes were not treated in accordance with the present invention;

FIG. 2 graphically shows the results of the effectiveness of treating hyperglycemia in fasting female and male rats having type I diabetes with DMF against a control group in which fasting female and male rats having type I diabetes were not treated in accordance with the present invention;

FIG. 3 graphically shows the effect of treatment with DMF with respect to cholesterol and triglyceride levels in female and male rats having type I diabetes, as against a known level of cholesterol and triglycerides in non-diabetic female and male rats;

FIG. 4 graphically shows the effect of treatment with DMF on renal function as represented by levels of urea and serum creatinine in female and male rats having type I diabetes, as against known levels of urea and serum creatinine in non-diabetic female and male rats; and, FIG. 5 graphically shows the effect on treatment with DMF on liver function as represented by levels of bilirubin, aspartate aminotransferase, gamma glutamyltransferase and alkaline phosphatase in female and male rats having type I diabetes, as against known levels of bilirubin, aspartate aminotransferase, gamma glutamyltransferase and alkaline phosphatase in non-diabetic female and male rats.

DETAILED DESCRIPTION OF DRAWING FIGURES AND CONTROLLED TEST RESULTS

Controlled test results were performed by, and under the direction of, the inventors, involving four type I diabetic rats, two of which were female and two were male, for the purpose of measuring the effectiveness of administering treatment in accordance with the present invention. Of the four rats involved in the controlled tests, one female and one male type I diabetic rats were treated with DMF with a daily dosage of 8 mg/kg body weight, intraperitoneally ("ip."). The remaining one female and one male type I diabetic rats remained untreated.

The results of testing included the following observations:

A first rat that was ultimately treated with DMF in accordance with the present invention was initially observed four weeks after STZ (streptozotocin)-induced diabetes and was determined to have an average level of glycemia of 440 mg %. Four days after treatment, the blood glucose level was measured and determined to be 94 mg % and the blood glucose level remained below 100 mg % after seven days of treatment.

A second rat that was ultimately treated with DMF in accordance with the present invention was initially observed four weeks after STZ (streptozotocin)-induced diabetes and was determined to have an average level of glycemia of 526 mg %. Four days after treatment, the blood glucose level was measured and determined to be 121 mg % and the blood glucose level remained below 120 mg % after seven days of treatment.

A third rat that was not treated with DMF in accordance with the present invention (and therefore a part of the control group) was initially observed four weeks after STZ (streptozotocin)-induced diabetes and was determined to have an average level of glycemia of 471 mg %. Its glycemia level continued to increase over the course of the testing and was observed as having an average glycemia level of 566 mg % during the period of controlled testing.

A fourth rat that was not treated with DMF in accordance with the present invention (and therefore a part of the control group) was initially observed four weeks after STZ (streptozotocin)-induced diabetes and was determined to have an average level of glycemia of 551 mg %. Its glycemia level continued to increase over the course of the testing and was observed as having an average glycemia level of 600 mg % during the period of controlled testing.

The results established that those rats in the test group that were treated with DMF in accordance with the method of the present invention had lowered levels of glycemia and maintained those lower glycemia levels throughout treatment, while rats in the control group, which were untreated after STZ-induced diabetes continued to have increasingly higher and higher glycemia levels throughout the test period.

The results of tests performed under the direction of the inventors are summarized in the graphs presented in the accompanying drawing figures. FIG. 1 shows treatment with DMF in accordance with the present invention having started during the first week of treatment for female and male type I diabetic rats with the glycemia level in both female and male rates receiving treatment remaining significantly below female and male rats not receiving treatment. FIG. 2 graphically shows a similar result for female and male rats in which fasting glycemia levels were measured.

FIG. 3 shows that cholesterol levels in the female and male rats treated with DMF in accordance with the present invention were somewhat elevated over the cholesterol levels of both the untreated rats and known levels in non-diabetic female and male rats, however triglycerides levels were significantly lowered, when compared to both the untreated female and male rats, as well as known levels of triglycerides present in female and male non-diabetic rats.

FIG. 4 graphically presents the results of renal function tests with female and male rats treated with DMF in accordance with the present invention having levels of urea and serum creatinine below that of the untreated type I diabetic rats in the test study and, in the case of serum creatinine levels, the levels of serum creatinine in female and male rats treated with DMF in accordance with the present invention were not only lower than the untreated, type I diabetic control group, but also lower than known levels of serum creatinine in non-diabetic female and male rats.

FIG. 5 presents the results of liver function tests with female and male rats, as represented by levels of bilirubin, aspartate aminotransferase, gamma glutamyltransferase and alkaline phosphatase. As graphically illustrated, in most instances, liver function was either improved or not substantially different as between the rats treated with DMF in accordance with the present invention and those rats in the control group which were untreated.

The results summarized in FIGS. 3, 4 and 5 also suggest that the administration of DMF in accordance with the method of the present invention could have effective applications beyond the treatment of hyperglycemic levels in human patients.

While only several embodiments of the present invention have been shown and described, it will be obvious to those skilled in the art that many modifications may be made to the present invention without departing from the spirit and scope thereof.

What is claimed is:

1. A method for treating a hyperglycemic condition, comprising the step of:
    administering dimethylformamide to a patient thereby reducing a glycemic level of the patient by providing the patient with a daily dosage of approximately 0.041 mg/kg body weight to approximately 1.23 mg/kg of body weight of the patient.

2. The method for treating a hyperglycemic condition, according to claim 1, wherein said step for administering dimethylformamide is performed by orally administering dimethylformamide to the patient.

3. The method for treating a hyperglycemic condition, according to claim 2, further comprising the step of:
    mixing dimethylformamide with an inert substance prior to said orally administering dimethylformamide to the patient.

4. The method for treating a hyperglycemic condition, according to claim 3, wherein said inert substance is a sugarless fruit juice concentrate with dimethylformamide being dissolved in the sugarless fruit juice concentrate.

5. The method for treating a hyperglycemic condition, according to claim 3, wherein said inert substance includes a sugar-free acidic liquid including an acid selected from the group consisting of citric acid, malic acid and a combination thereof, with dimethylformamide dissolved in the sugar-free acidic liquid.

6. A method for treating a hyperglycemic condition, comprising the steps of:
    mixing dimethylformamide with an inert substance, wherein said inert substance is a sugarless fruit juice concentrate with dimethylformamide being dissolved in the sugarless fruit juice concentrate; and,
    orally administering dimethylformamide with said inert substance mixed therewith to a patient thereby reducing a glycemic level of the patient.

7. The method for treating a hyperglycemic condition according to claim 6, wherein said inert substance includes a sugar-free acidic liquid including an acid selected from the group consisting of citric acid, malic acid and a combination thereof, with dimethylformamide dissolved in the sugar-free acidic liquid.

* * * * *